United States Patent
Biberger et al.

(10) Patent No.: US 8,575,059 B1
(45) Date of Patent: Nov. 5, 2013

(54) METHOD AND SYSTEM FOR FORMING PLUG AND PLAY METAL COMPOUND CATALYSTS

(75) Inventors: Maximilian A. Biberger, Scottsdale, AZ (US); Stephen Edward Lehman, Jr., Chandler, AZ (US); Robert Matthew Kevwitch, Chandler, AZ (US); Qinghua Yin, Tempe, AZ (US); Jesudos J. Kingsley, Scottsdale, AZ (US)

(73) Assignee: SDCmaterials, Inc., Tempe, AZ (US)

( * ) Notice: Subject to any disclaimer, the term of this patent is extended or adjusted under 35 U.S.C. 154(b) by 0 days.

(21) Appl. No.: 12/001,602

(22) Filed: Dec. 11, 2007

Related U.S. Application Data

(60) Provisional application No. 60/999,057, filed on Oct. 15, 2007.

(51) Int. Cl.
| | | |
|---|---|---|
| B01J 21/00 | (2006.01) | |
| B32B 15/02 | (2006.01) | |
| B05D 1/36 | (2006.01) | |
| B05D 3/02 | (2006.01) | |
| B05D 3/00 | (2006.01) | |

(52) U.S. Cl.
USPC ........... 502/232; 428/402; 428/403; 427/201; 427/229; 427/398.1

(58) Field of Classification Search
None
See application file for complete search history.

(56) References Cited

U.S. PATENT DOCUMENTS

| | | | |
|---|---|---|---|
| 2,284,554 A | 5/1942 | Beyerstedt | ...................... 196/10 |
| 2,419,042 A | 4/1947 | Todd | |
| 2,519,531 A | 8/1950 | Worn | ............................... 230/95 |
| 2,562,753 A | 7/1951 | Trost | |
| 2,689,780 A | 9/1954 | Rice | |
| 3,001,402 A | 9/1961 | Koblin | ......................... 73/421.5 |
| 3,067,025 A | 12/1962 | Chisholm | |
| 3,145,287 A | 8/1964 | Siebein et al. | |
| 3,178,121 A | 4/1965 | Wallace, Jr. | |
| 3,179,782 A | 4/1965 | Matvay | |
| 3,313,908 A | 4/1967 | Unger et al. | |
| 3,401,465 A | 9/1968 | Larwill | |

(Continued)

FOREIGN PATENT DOCUMENTS

| | | | |
|---|---|---|---|
| JP | 56-146804 A | 11/1981 | |
| JP | 61-086815 A | 5/1986 | |

(Continued)

OTHER PUBLICATIONS

Kenvin et al., Journal of Catalysis, v. 135, p. 81-91, May 1992.*

(Continued)

*Primary Examiner* — Milton I Cano
*Assistant Examiner* — Sarah A Slifka
(74) *Attorney, Agent, or Firm* — Morrison & Foerster LLP

(57) ABSTRACT

A metal compound catalyst is formed by vaporizing a quantity of catalyst material and a quantity of carrier thereby forming a vapor cloud, exposing the vapor cloud to a co-reactant and quenching the vapor cloud. The nanoparticles are impregnated onto supports. The supports are able to be used in existing heterogeneous catalysis systems. A system for forming metal compound catalysts comprises components for vaporizing a quantity of catalyst material and a quantity of carrier, quenching the resulting vapor cloud, forming precipitate nanoparticles comprising a portion of catalyst material and a portion of carrier, and subjecting the nanoparticles to a co-reactant. The system further comprises components for impregnating the supports with the nanoparticles.

19 Claims, 7 Drawing Sheets

(56) References Cited

U.S. PATENT DOCUMENTS

| | | |
|---|---|---|
| 3,450,926 A | 6/1969 | Kiernan .................... 313/231 |
| 3,457,788 A | 7/1969 | Miyajima .................... 73/422 |
| 3,537,513 A | 11/1970 | Austin |
| 3,741,001 A | 6/1973 | Fletcher et al. .................... 73/28 |
| 3,752,172 A | 8/1973 | Cohen et al. |
| 3,774,442 A | 11/1973 | Gustavsson .................... 73/28 |
| 3,830,756 A | 8/1974 | Sanchez et al. |
| 3,871,448 A | 3/1975 | Vann et al. |
| 3,892,882 A | 7/1975 | Guest et al. |
| 3,914,573 A | 10/1975 | Muehlberger |
| 3,959,420 A | 5/1976 | Geddes et al. .................... 261/112 |
| 3,969,482 A | 7/1976 | Teller |
| 4,008,620 A | 2/1977 | Narato et al. .................... 73/421.5 A |
| 4,018,388 A | 4/1977 | Andrews |
| 4,139,497 A | 2/1979 | Castor et al. |
| 4,157,316 A | 6/1979 | Thompson et al. |
| 4,171,288 A * | 10/1979 | Keith et al. .................... 502/304 |
| 4,174,298 A | 11/1979 | Antos |
| 4,227,928 A | 10/1980 | Wang |
| 4,248,387 A | 2/1981 | Andrews |
| 4,253,917 A | 3/1981 | Wang |
| 4,284,609 A | 8/1981 | deVries |
| 4,369,167 A | 1/1983 | Weir |
| 4,388,274 A | 6/1983 | Rourke et al. |
| 4,431,750 A | 2/1984 | McGinnis et al. |
| 4,436,075 A | 3/1984 | Campbell et al. |
| 4,458,138 A | 7/1984 | Adrian et al. |
| 4,459,327 A | 7/1984 | Wang |
| 4,505,945 A | 3/1985 | Dubust et al. |
| 4,513,149 A | 4/1985 | Gray et al. |
| 4,731,517 A | 3/1988 | Cheney |
| 4,764,283 A | 8/1988 | Ashbrook et al. |
| 4,765,805 A | 8/1988 | Wahl et al. |
| 4,824,624 A | 4/1989 | Palicka et al. .................... 264/67 |
| 4,855,505 A | 8/1989 | Koll |
| 4,866,240 A | 9/1989 | Webber |
| 4,885,038 A | 12/1989 | Anderson et al. |
| 4,983,555 A | 1/1991 | Roy et al. .................... 501/120 |
| 4,987,033 A | 1/1991 | Abkowitz et al. .................... 428/469 |
| 5,015,863 A | 5/1991 | Takeshima et al. |
| 5,041,713 A | 8/1991 | Weidman |
| 5,043,548 A | 8/1991 | Whitney et al. |
| 5,070,064 A | 12/1991 | Hsu et al. |
| 5,073,193 A | 12/1991 | Chaklader et al. .................... 75/346 |
| 5,157,007 A | 10/1992 | Domesle et al. |
| 5,230,844 A | 7/1993 | Macaire et al. |
| 5,338,716 A | 8/1994 | Triplett et al. |
| 5,369,241 A | 11/1994 | Taylor et al. .................... 219/121.47 |
| 5,371,049 A | 12/1994 | Moffett et al. .................... 501/89 |
| 5,372,629 A | 12/1994 | Anderson et al. .................... 75/332 |
| 5,392,797 A | 2/1995 | Welch .................... 134/108 |
| 5,439,865 A | 8/1995 | Abe et al. |
| 5,442,153 A | 8/1995 | Marantz et al. |
| 5,460,701 A | 10/1995 | Parker et al. |
| 5,464,458 A | 11/1995 | Yamamoto |
| 5,485,941 A | 1/1996 | Guyomard et al. .................... 222/1 |
| 5,534,149 A | 7/1996 | Birkenbeil et al. |
| 5,553,507 A | 9/1996 | Basch et al. .................... 73/863.01 |
| 5,562,966 A | 10/1996 | Clarke et al. |
| 5,582,807 A | 12/1996 | Liao et al. |
| 5,611,896 A | 3/1997 | Swanepoel et al. .................... 204/169 |
| 5,630,322 A | 5/1997 | Heilmann et al. .................... 62/95 |
| 5,652,304 A | 7/1997 | Mizrahi |
| 5,726,414 A | 3/1998 | Kitahashi et al. |
| 5,749,938 A | 5/1998 | Coombs .................... 75/332 |
| 5,776,359 A | 7/1998 | Schultz et al. .................... 252/62.51 |
| 5,788,738 A | 8/1998 | Pirzada et al. .................... 75/331 |
| 5,811,187 A | 9/1998 | Anderson et al. .................... 428/403 |
| 5,837,959 A | 11/1998 | Muehlberger et al. |
| 5,851,507 A | 12/1998 | Pirzada et al. |
| 5,853,815 A | 12/1998 | Muehlberger |
| 5,905,000 A | 5/1999 | Yadav et al. .................... 429/33 |
| 5,935,293 A | 8/1999 | Detering et al. .................... 75/10.29 |
| 5,989,648 A | 11/1999 | Phillips .................... 427/456 |
| 5,993,967 A | 11/1999 | Brotzman, Jr. et al. .................... 428/407 |
| 5,993,988 A | 11/1999 | Ohara et al. .................... 429/40 |
| 6,012,647 A | 1/2000 | Ruta et al. |
| 6,033,781 A | 3/2000 | Brotzman, Jr. et al. .................... 428/405 |
| 6,045,765 A | 4/2000 | Nakatsuji et al. |
| 6,059,853 A | 5/2000 | Coombs .................... 75/332 |
| 6,102,106 A | 8/2000 | Manning et al. |
| 6,117,376 A | 9/2000 | Merkel |
| 6,213,049 B1 | 4/2001 | Yang |
| 6,214,195 B1 | 4/2001 | Yadav et al. .................... 205/334 |
| 6,228,904 B1 | 5/2001 | Yadav et al. .................... 523/210 |
| 6,254,940 B1 | 7/2001 | Pratsinis et al. .................... 427/562 |
| 6,261,484 B1 | 7/2001 | Phillips et al. .................... 264/5 |
| 6,267,864 B1 | 7/2001 | Yadav et al. .................... 205/341 |
| 6,322,756 B1 | 11/2001 | Arno et al. |
| 6,342,465 B1 | 1/2002 | Klein et al. |
| 6,344,271 B1 | 2/2002 | Yadav et al. .................... 428/402 |
| 6,379,419 B1 | 4/2002 | Celik et al. .................... 75/346 |
| 6,387,560 B1 | 5/2002 | Yadav et al. .................... 429/45 |
| 6,395,214 B1 | 5/2002 | Kear et al. .................... 264/434 |
| 6,398,843 B1 | 6/2002 | Tarrant .................... 75/249 |
| 6,409,851 B1 | 6/2002 | Sethuram et al. .................... 148/565 |
| 6,413,781 B1 | 7/2002 | Geis et al. |
| 6,416,818 B1 | 7/2002 | Aikens et al. .................... 427/383.1 |
| RE37,853 E | 9/2002 | Detering et al. .................... 75/10.19 |
| 6,444,009 B1 | 9/2002 | Liu et al. .................... 75/332 |
| 6,475,951 B1 | 11/2002 | Domesle et al. |
| 6,517,800 B1 | 2/2003 | Cheng et al. .................... 423/447.1 |
| 6,524,662 B2 | 2/2003 | Jang et al. .................... 427/535 |
| 6,531,704 B2 | 3/2003 | Yadav et al. .................... 250/493.1 |
| 6,548,445 B1 | 4/2003 | Buysch et al. |
| 6,554,609 B2 | 4/2003 | Yadav et al. .................... 432/9 |
| 6,562,304 B1 | 5/2003 | Mizrahi |
| 6,562,495 B2 | 5/2003 | Yadav et al. .................... 429/12 |
| 6,569,397 B1 | 5/2003 | Yadav et al. .................... 423/345 |
| 6,569,518 B2 | 5/2003 | Yadav et al. .................... 428/323 |
| 6,572,672 B2 | 6/2003 | Yadav et al. .................... 75/343 |
| 6,579,446 B1 | 6/2003 | Teran et al. |
| 6,596,187 B2 | 7/2003 | Coll et al. |
| 6,603,038 B1 | 8/2003 | Hagemeyer et al. |
| 6,607,821 B2 | 8/2003 | Yadav et al. .................... 428/323 |
| 6,610,355 B2 | 8/2003 | Yadav et al. .................... 427/115 |
| 6,623,559 B2 | 9/2003 | Huang |
| 6,635,357 B2 | 10/2003 | Moxson et al. .................... 428/548 |
| 6,641,775 B2 | 11/2003 | Vigliotti et al. .................... 264/618 |
| 6,652,822 B2 | 11/2003 | Phillips et al. .................... 423/290 |
| 6,652,967 B2 * | 11/2003 | Yadav et al. .................... 428/403 |
| 6,669,823 B1 | 12/2003 | Sarkas et al. .................... 204/164 |
| 6,682,002 B2 | 1/2004 | Kyotani .................... 239/318 |
| 6,689,192 B1 | 2/2004 | Phillips et al. .................... 75/342 |
| 6,699,398 B1 | 3/2004 | Kim .................... 216/55 |
| 6,706,097 B2 | 3/2004 | Zornes .................... 96/153 |
| 6,706,660 B2 | 3/2004 | Park |
| 6,710,207 B2 | 3/2004 | Bogan, Jr. et al. |
| 6,713,176 B2 | 3/2004 | Yadav et al. .................... 428/402 |
| 6,716,525 B1 | 4/2004 | Yadav et al. .................... 428/402 |
| 6,746,791 B2 | 6/2004 | Yadav et al. .................... 429/30 |
| 6,772,584 B2 | 8/2004 | Chun et al. .................... 60/275 |
| 6,786,950 B2 | 9/2004 | Yadav et al. .................... 75/346 |
| 6,813,931 B2 | 11/2004 | Yadav et al. .................... 73/31.05 |
| 6,817,388 B2 | 11/2004 | Tsangaris et al. .................... 141/82 |
| 6,832,735 B2 | 12/2004 | Yadav et al. .................... 241/16 |
| 6,838,072 B1 | 1/2005 | Kong et al. .................... 423/594.2 |
| 6,855,410 B2 | 2/2005 | Buckley |
| 6,855,426 B2 | 2/2005 | Yadav .................... 428/403 |
| 6,855,749 B1 | 2/2005 | Yadav et al. .................... 523/105 |
| 6,886,545 B1 | 5/2005 | Holm .................... 123/568.21 |
| 6,896,958 B1 | 5/2005 | Cayton et al. .................... 428/323 |
| 6,902,699 B2 | 6/2005 | Fritzemeier et al. .................... 419/38 |
| 6,916,872 B2 | 7/2005 | Yadav et al. .................... 524/430 |
| 6,919,527 B2 | 7/2005 | Boulos et al. .................... 219/121.52 |
| 6,933,331 B2 | 8/2005 | Yadav et al. .................... 523/210 |
| 6,972,115 B1 | 12/2005 | Ballard |
| 6,986,877 B2 | 1/2006 | Takikawa et al. .................... 423/447.3 |
| 6,994,837 B2 | 2/2006 | Boulos et al. .................... 423/613 |
| 7,007,872 B2 | 3/2006 | Yadav et al. .................... 241/1 |
| 7,022,305 B2 | 4/2006 | Drumm et al. |
| 7,052,777 B2 | 5/2006 | Brotzman, Jr. et al. .................... 428/570 |
| 7,073,559 B2 | 7/2006 | O'Larey et al. .................... 164/76.1 |
| 7,081,267 B2 | 7/2006 | Yadav .................... 427/115 |

(56) References Cited

U.S. PATENT DOCUMENTS

| | | | |
|---|---|---|---|
| 7,101,819 B2 | 9/2006 | Rosenflanz et al. | 501/10 |
| 7,147,544 B2 | 12/2006 | Rosenflanz | 451/28 |
| 7,147,894 B2 | 12/2006 | Zhou et al. | 427/256 |
| 7,166,198 B2 | 1/2007 | Van Der Walt et al. | 204/165 |
| 7,166,663 B2 | 1/2007 | Cayton et al. | 524/430 |
| 7,172,649 B2 | 2/2007 | Conrad et al. | 106/35 |
| 7,172,790 B2 | 2/2007 | Koulik et al. | 427/212 |
| 7,178,747 B2 | 2/2007 | Yadav et al. | 241/23 |
| 7,208,126 B2 | 4/2007 | Musick et al. | 423/69 |
| 7,211,236 B2 | 5/2007 | Stark et al. | 423/592.1 |
| 7,217,407 B2 | 5/2007 | Zhang | 423/610 |
| 7,220,398 B2 | 5/2007 | Sutorik et al. | |
| 7,307,195 B2 | 12/2007 | Polverejan et al. | 585/443 |
| 7,323,655 B2 | 1/2008 | Kim | 219/121.43 |
| 7,384,447 B2 | 6/2008 | Kodas et al. | 75/332 |
| 7,417,008 B2 | 8/2008 | Richards et al. | |
| 7,494,527 B2 | 2/2009 | Jurewicz et al. | |
| 7,541,012 B2 | 6/2009 | Yeung et al. | |
| 7,541,310 B2 | 6/2009 | Espinoza et al. | |
| 7,572,315 B2 | 8/2009 | Boulos et al. | |
| 7,611,686 B2 | 11/2009 | Alekseeva et al. | |
| 7,615,097 B2 | 11/2009 | McKechnie et al. | |
| 7,618,919 B2 | 11/2009 | Shimazu et al. | |
| 7,622,693 B2 | 11/2009 | Foret | |
| 7,678,419 B2 | 3/2010 | Kevwitch et al. | |
| 7,803,210 B2 | 9/2010 | Sekine et al. | |
| 7,874,239 B2 | 1/2011 | Howland | |
| 7,897,127 B2 | 3/2011 | Layman et al. | |
| 7,905,942 B1 | 3/2011 | Layman | |
| 8,051,724 B1 | 11/2011 | Layman et al. | |
| 8,076,258 B1 | 12/2011 | Biberger | |
| 8,142,619 B2 | 3/2012 | Layman et al. | |
| 2001/0042802 A1 | 11/2001 | Youds | |
| 2002/0018815 A1 | 2/2002 | Sievers et al. | |
| 2002/0068026 A1 | 6/2002 | Murrell et al. | |
| 2002/0079620 A1 | 6/2002 | DuBuis et al. | 264/328.14 |
| 2002/0100751 A1 | 8/2002 | Carr | |
| 2002/0102674 A1 | 8/2002 | Anderson | |
| 2002/0131914 A1 | 9/2002 | Sung | |
| 2002/0143417 A1 | 10/2002 | Ito et al. | |
| 2002/0182735 A1 | 12/2002 | Kibby et al. | |
| 2002/0183191 A1 | 12/2002 | Faber et al. | |
| 2002/0192129 A1 | 12/2002 | Shamouilian et al. | |
| 2003/0036786 A1 | 2/2003 | Duren et al. | |
| 2003/0042232 A1 | 3/2003 | Shimazu | |
| 2003/0066800 A1 | 4/2003 | Saim et al. | |
| 2003/0072677 A1 | 4/2003 | Kafesjian et al. | |
| 2003/0108459 A1 | 6/2003 | Wu et al. | 422/186.04 |
| 2003/0110931 A1 | 6/2003 | Aghajanian et al. | |
| 2003/0139288 A1 | 7/2003 | Cai et al. | |
| 2003/0143153 A1 | 7/2003 | Boulos et al. | |
| 2003/0172772 A1 | 9/2003 | Sethuram et al. | |
| 2003/0223546 A1 | 12/2003 | McGregor et al. | 378/143 |
| 2004/0009118 A1 | 1/2004 | Phillips et al. | |
| 2004/0023302 A1 | 2/2004 | Archibald et al. | |
| 2004/0023453 A1 | 2/2004 | Xu et al. | |
| 2004/0064964 A1 | 4/2004 | Lee | |
| 2004/0077494 A1 | 4/2004 | LaBarge et al. | |
| 2004/0103751 A1 | 6/2004 | Joseph et al. | |
| 2004/0119064 A1 | 6/2004 | Narayan et al. | |
| 2004/0127586 A1 | 7/2004 | Jin et al. | |
| 2004/0167009 A1 | 8/2004 | Kuntz et al. | 501/95.2 |
| 2004/0176246 A1 | 9/2004 | Shirk et al. | |
| 2004/0208805 A1 | 10/2004 | Fincke et al. | |
| 2004/0213998 A1 | 10/2004 | Hearley et al. | |
| 2004/0238345 A1 | 12/2004 | Koulik et al. | |
| 2004/0251017 A1 | 12/2004 | Pillion et al. | |
| 2004/0251241 A1 | 12/2004 | Blutke et al. | |
| 2005/0000321 A1 | 1/2005 | O'Larey et al. | 75/952 |
| 2005/0000950 A1 | 1/2005 | Schroder et al. | 219/121.59 |
| 2005/0066805 A1 | 3/2005 | Park et al. | |
| 2005/0077034 A1 | 4/2005 | King | |
| 2005/0097988 A1 | 5/2005 | Kodas et al. | 75/332 |
| 2005/0106865 A1 | 5/2005 | Chung et al. | |
| 2005/0163673 A1 | 7/2005 | Johnson et al. | |
| 2005/0199739 A1 | 9/2005 | Kuroda et al. | |
| 2005/0220695 A1 | 10/2005 | Abatzoglou et al. | |
| 2005/0227864 A1 | 10/2005 | Sutorik et al. | |
| 2005/0233380 A1 | 10/2005 | Pesiri et al. | |
| 2005/0240069 A1 | 10/2005 | Polverejan et al. | 585/444 |
| 2005/0258766 A1 | 11/2005 | Kim | 315/111.21 |
| 2005/0275143 A1 | 12/2005 | Toth | |
| 2006/0051505 A1 | 3/2006 | Kortshagen et al. | 427/212 |
| 2006/0068989 A1 | 3/2006 | Ninomiya et al. | |
| 2006/0094595 A1 | 5/2006 | Labarge | |
| 2006/0096393 A1 | 5/2006 | Pesiri | 73/863.21 |
| 2006/0105910 A1* | 5/2006 | Zhou et al. | 502/338 |
| 2006/0108332 A1 | 5/2006 | Belashchenko | 219/121.47 |
| 2006/0153728 A1 | 7/2006 | Schoenung et al. | |
| 2006/0153765 A1* | 7/2006 | Pham-Huu et al. | 423/345 |
| 2006/0159596 A1 | 7/2006 | De La Veaux et al. | 422/151 |
| 2006/0166809 A1 | 7/2006 | Malek et al. | |
| 2006/0222780 A1 | 10/2006 | Gurevich et al. | |
| 2006/0231525 A1 | 10/2006 | Asakawa et al. | 216/56 |
| 2007/0048206 A1 | 3/2007 | Hung et al. | |
| 2007/0049484 A1 | 3/2007 | Kear et al. | |
| 2007/0063364 A1 | 3/2007 | Hsiao et al. | 264/5 |
| 2007/0084308 A1 | 4/2007 | Nakamura et al. | |
| 2007/0084834 A1 | 4/2007 | Hanus et al. | |
| 2007/0087934 A1 | 4/2007 | Martens et al. | 502/214 |
| 2007/0163385 A1 | 7/2007 | Takahashi et al. | |
| 2007/0173403 A1 | 7/2007 | Koike et al. | |
| 2007/0178673 A1 | 8/2007 | Gole et al. | |
| 2007/0253874 A1 | 11/2007 | Foret | |
| 2007/0292321 A1 | 12/2007 | Plischke et al. | |
| 2008/0006954 A1 | 1/2008 | Yubuta et al. | |
| 2008/0031806 A1 | 2/2008 | Gavenonis et al. | |
| 2008/0038578 A1 | 2/2008 | Li | |
| 2008/0064769 A1 | 3/2008 | Sato et al. | |
| 2008/0105083 A1 | 5/2008 | Nakamura et al. | |
| 2008/0116178 A1 | 5/2008 | Weidman | |
| 2008/0125308 A1 | 5/2008 | Fujdala et al. | |
| 2008/0138651 A1 | 6/2008 | Doi et al. | |
| 2008/0175936 A1 | 7/2008 | Tokita et al. | |
| 2008/0206562 A1 | 8/2008 | Stucky et al. | |
| 2008/0207858 A1 | 8/2008 | Kowaleski et al. | 526/176 |
| 2008/0274344 A1 | 11/2008 | Vieth et al. | |
| 2008/0277092 A1 | 11/2008 | Layman et al. | |
| 2008/0277264 A1 | 11/2008 | Biberger et al. | |
| 2008/0277266 A1 | 11/2008 | Layman | |
| 2008/0277267 A1 | 11/2008 | Biberger et al. | |
| 2008/0277268 A1 | 11/2008 | Layman | |
| 2008/0277269 A1 | 11/2008 | Layman et al. | |
| 2008/0277270 A1 | 11/2008 | Biberger et al. | |
| 2008/0277271 A1 | 11/2008 | Layman | |
| 2008/0280049 A1 | 11/2008 | Kevwitch et al. | |
| 2008/0280751 A1 | 11/2008 | Harutyunyan et al. | |
| 2008/0280756 A1 | 11/2008 | Layman | |
| 2009/0010801 A1 | 1/2009 | Murphy et al. | |
| 2009/0054230 A1 | 2/2009 | Veeraraghavan et al. | |
| 2009/0088585 A1 | 4/2009 | Schammel et al. | |
| 2009/0114568 A1 | 5/2009 | Trevino et al. | |
| 2009/0162991 A1 | 6/2009 | Beneyton et al. | |
| 2009/0168506 A1 | 7/2009 | Han et al. | |
| 2009/0170242 A1 | 7/2009 | Lin et al. | |
| 2009/0181474 A1 | 7/2009 | Nagai | |
| 2009/0200180 A1 | 8/2009 | Capote et al. | |
| 2009/0253037 A1 | 10/2009 | Park et al. | |
| 2009/0274903 A1 | 11/2009 | Addiego | |
| 2009/0286899 A1 | 11/2009 | Hofmann et al. | |
| 2010/0089002 A1 | 4/2010 | Merkel | |
| 2010/0275781 A1 | 11/2010 | Tsangaris | |
| 2011/0006463 A1 | 1/2011 | Layman | |
| 2011/0143041 A1 | 6/2011 | Layman et al. | |
| 2011/0143915 A1 | 6/2011 | Yin et al. | |
| 2011/0143916 A1 | 6/2011 | Leamon | |
| 2011/0143926 A1 | 6/2011 | Leamon | |
| 2011/0143930 A1 | 6/2011 | Yin et al. | |
| 2011/0143933 A1 | 6/2011 | Yin et al. | |
| 2011/0144382 A1 | 6/2011 | Yin et al. | |
| 2011/0152550 A1 | 6/2011 | Grey et al. | |
| 2011/0158871 A1 | 6/2011 | Arnold et al. | |
| 2011/0174604 A1 | 7/2011 | Duesel et al. | |

(56) References Cited

U.S. PATENT DOCUMENTS

| | | | |
|---|---|---|---|
| 2011/0247336 | A9 | 10/2011 | Farsad et al. |
| 2012/0045373 | A1 | 2/2012 | Biberger |
| 2012/0171098 | A1 | 7/2012 | Hung et al. |

FOREIGN PATENT DOCUMENTS

| | | | |
|---|---|---|---|
| JP | 63-214342 A | 9/1988 | |
| JP | 05-228361 A | 9/1993 | |
| JP | 05-324094 A | 12/1993 | |
| JP | H6-065772 | 9/1994 | |
| JP | 7031873 A | 2/1995 | |
| JP | 07-256116 | 10/1995 | |
| JP | 11-502760 A | 3/1999 | |
| JP | 2000-220978 A | 8/2000 | |
| JP | 2004-233007 A | 8/2004 | |
| JP | 2004-249206 A | 9/2004 | |
| JP | 2004-290730 A | 10/2004 | |
| JP | 2005-503250 A | 2/2005 | |
| JP | 2005-122621 A | 5/2005 | |
| JP | 2005-218937 A | 8/2005 | |
| JP | 2005-342615 A | 12/2005 | |
| JP | 2006-001779 A | 1/2006 | |
| JP | 2006-508885 A | 3/2006 | |
| JP | 2006-247446 A | 9/2006 | |
| JP | 2006-260385 A | 9/2006 | |
| SU | 493241 | 3/1976 | |
| TW | 201023207 | 6/2010 | |
| WO | WO-96/28577 A1 | 9/1996 | |
| WO | WO 02/092503 A1 | 11/2002 | |
| WO | 2004052778 A2 | 6/2004 | |
| WO | WO 2006/079213 A1 | 8/2006 | |
| WO | WO-2008/130451 A2 | 10/2008 | |
| WO | WO-2008/130451 A3 | 10/2008 | |

OTHER PUBLICATIONS

J. Heberlein, "New Approaches in Thermal Plasma Technology", Pure Appl. Chem., vol. 74, No. 3, 2002, pp. 327-335.

T. Yoshida, "The Future of Thermal Plasma Processing for Coating", Pure & Appl. Chem., vol. 66, No. 6, 1994 pp. 1223-1230.

A. Gutsch et al., "Gas-Phase Production of Nanoparticles", Kona No. 20, 2002, pp. 24-37.

Dr. Heike Mühlenweg et al., "Gas-Phase Reactions—Open Up New Roads to Nanoproducts", Degussa ScienceNewsletter No. 08, 2004, pp. 12-16.

Coating Generation: Vaporization of Particles in Plasma Spraying and Splat Formation, M. Vardelle, A. Vardelle, K-I Ii, P. Fauchais, Universite de Limoges, 123 Avenue A. Thomas 87000, Limoges, F. , Pure & Chem, vol. 68, No. 5, pp. 1093-1099, 1996.

H. Konrad et al., "Nanostructured Cu—Bi Alloys Prepared by Co-Evaporation in a Continuous Gas Flow," NanoStructured Materials, vol. 7, No. 6, Apr. 1996, pp. 605-610.

M.Vardelle et al., "Experimental Investigation of Powder Vaporization in Thermal Plasma Jets," Plasma Chemistry and Plasma Processing, vol. 11, No. 2, Jun. 1991, pp. 185-201.

P. Fauchais et al., "Plasma Spray: Study of the Coating Generation," Ceramics International, Elsevier, Amsterdam, NL, vol. 22, No. 4, Jan. 1996, pp. 295-303.

P. Fauchais et al., "Les Dépôts Par Plasma Thermique," Revue Generale De L'Electricitie, RGE. Paris, FR, No. 2, Jan. 1993, pp. 7-12.

P. Fauchais et al, "La Projection Par Plasma: Une Revue," Annales De Physique, vol. 14, No. 3, Jun. 1989, pp. 261-310.

National Aeronautics and Space Administration, "Enthalpy", http://www.grc.nasa.gov/WWW/K-12/airplane/enthalpy.html, Nov. 23, 2009, 1 page.

Han et al., Deformation Mechanisms and Ductility of Nanostructured Al Alloys, Mat. Res. Soc. Symp. Proc. vol. 821, Jan. 2004, Material Research Society, http://www.mrs.org/s_mrs/bin.asp?CID=2670&DOC=FILE.PDF., 6 pages.

United States Patent and Trademark Office, Office Action, mailed Jan. 7, 2010, U.S. Appl. No. 12/001,643, filed Dec. 11, 2007, First Named Inventor: Maximilian A. Biberger, 8 pages.

United States Patent and Trademark Office, Office Action, mailed Feb. 18, 2010, U.S. Appl. No. 12/001,644, filed Dec. 11, 2007, First Named Inventor: Maximilian A. Biberger, 7 pages.

United States Patent and Trademark Office, Office Action, mailed Feb. 19, 2010, U.S. Appl. No. 12/152,109, filed May 9, 2008, First Named Inventor: Maximilian A. Biberger, 17 pages.

United States Patent and Trademark Office, Advisory Action, Mailed Mar. 4, 2010, U.S. Appl. No. 12/001,643, filed Dec. 11, 2007, First Named Inventor: Maximilian A. Biberger, pp. 9.

Untied States Patent and Trademark Office, Office Action, Mailed: Feb. 26, 2010, U.S. Appl. No. 12/474,081, filed May 28, 2009, First Named Inventor: Maximilian A. Biberger, 7 pages.

Untied States Patent and Trademark Office, Advisory Action, Mailed: May 4, 2010, U.S. Appl. No. 12/474,081, filed May 28, 2009, First Named Inventor: Maximilian A. Biberger, 4 pages.

Untied States Patent and Trademark Office, Office Action, Mailed Jun. 16, 2010, U.S. Appl. No. 12/001,643, filed Dec. 11, 2007, First Named Inventor: Maximilian A. Biberger, 8 pages.

Untied States Patent and Trademark Office, Office Action, Mailed Jun. 30, 2010, U.S. Appl. No. 12/001,644, filed Dec. 11, 2007, First Named Inventor: Maximilian A. Biberger, 8 pages.

Untied States Patent and Trademark Office, Office Action, Mailed Jun. 23, 2010, U.S. Appl. No. 12/474,081, filed May 28, 2009, First Named Inventor: Maximilian A. Biberger, 11 pages.

Derwent English Abstract for Publication No. SU 193241 A, Application No. 1973SU1943286 filed on Jul. 2, 1973, published on Mar. 1, 1976, entitled "Catalyst for Ammonia Synthesis Contains Oxides of Aluminium, Potassium, Calcium, Iron and Nickel Oxide for Increased Activity," 3 pgs.

Nagai, Yasutaka, et al., "Sintering Inhibition Mechanism of Platinum Supported on Ceria-based Oxide and Pt-oxide-support Interaction," Journal of Catalysis 242 (2006), pp. 103-109, Jul. 3, 2006, Elsevier.

United States Patent and Trademark Office, Office Action mailed. Dec. 8, 2010, for U.S. Appl. No. 12/474,081, pp. 1-13.

Advisory action dated Sep. 23, 2011, U.S. Appl. No. 12/001,643, filed Dec. 11, 2007, Applicant: Maximilian A. Biberger, 8 pages.

United States Patent and Trademark Office, Office Action mailed Jun. 21, 2011, for U.S. Appl. No. 12/001,644, 12 pgs.

United States Patent and Trademark Office, Office Action mailed Jun. 22, 2011, for U.S. Appl. No. 12/001,643, 13 pgs.

Bateman, James E. et al., "Alkylation of Porous Silicon by Direct Reaction with Alkenes and Alkynes," Angew. Chem Int. Ed., Dec. 17, 1998, 37, No. 19, pp. 2683-2685.

Langner, Alexander et al., "Controlled Silicon Surface Functionalization by Alkene Hydrosilylation," J. Am. Chem. Soc., Aug. 25, 2005, 127, pp. 12798-12799.

Liu, Shu-Man et al., "Enhanced Photoluminescence from Si Nano-organosols by Functionalization with Alkenes and Their Size Evolution," Chem. Mater., Jan. 13, 2006, 18, pp. 637-642.

Fojtik, Anton, "Surface Chemistry of Luminescent Colloidal Silicon Nanoparticles," J. Phys. Chem. B., Jan. 13, 2006, pp. 1994-1998.

Li, Dejin et al., "Environmentally Responsive "Hairy" Nanoparticles: Mixed Homopolymer Brushes on Silica Nanoparticles Synthesized by Living Radical Polymerization Techniques," J.Am. Chem. Soc., Apr. 9, 2005, 127,pp. 6248-6256.

Neiner, Doinita, "Low-Temperature Solution Route to Macroscopic Amounts of Hydrogen Terminated Silicon Nanoparticles," J. Am. Chem. Soc., Aug. 5, 2006, 128, pp. 11016-11017.

Fojtik, Anton et al., "Luminescent Colloidal Silicon Particles," Chemical Physics Letters 221, Apr. 29, 1994, pp. 363-367.

Netzer, Lucy et al., "A New Approach to Construction of Artificial Monolayer Assemblies," J. Am. Chem. Soc., 1983, 105, pp. 674-676.

Chen, H.-S. et al., "On the Photoluminescence of Si Nanoparticles," Mater. Phys. Mech. 4, Jul. 3, 2001, pp. 62-66.

Kwon, Young-Soon et al., "Passivation Process for Superfine Aluminum Powders Obtained by Electrical Explosion of Wires," Applied Surface Science 211, Apr. 30, 2003, pp. 57-67.

Liao, Ying-Chih et al., "Self-Assembly of Organic Monolayers on Aerosolized Silicon Nanoparticles," J.Am. Chem. Soc., Jun. 27, 2006, 128, pp. 9061-9065.

(56) References Cited

OTHER PUBLICATIONS

Zou, Jing et al., "Solution Synthesis of Ultrastable Luminescent Siloxane-Coated Silicon Nanoparticles," Nano Letters, Jun. 4, 2004, vol. 4, No. 7, pp. 1181-1186.

Tao, Yu-Tai, "Structural Comparison of Self-Assembled Monolayers of n-Alkanoic Acids on the surfaces of Silver, Copper, and Aluminum," J. Am. Chem. Soc., May 1993, 115, pp. 4350-4358.

Sailor, Michael et al., "Surface Chemistry of Luminescent Silicon Nanocrystallites," Adv. Mater, 1997, 9, No. 10, pp. 783-793.

Li, Xuegeng et al., "Surface Functionalization of Silicon Nanoparticles Produced by Laser-Driven Pyrolysis of Silane Followed by HF-HNO3 Etching," Langmuir, May 25, 2004, pp. 4720-4727.

Carrot, Geraldine et al., "Surface-Initiated Ring-Opening Polymerization: A Versatile Method for Nanoparticle Ordering," Macromolecules, Sep. 17, 2002, 35, pp. 8400-8404.

Jouet, R. Jason et al., "Surface Passivation of Bare Aluminum Nanoparticles Using Perfluoroalkyl Carboxylic Acids," Chem. Mater., Jan. 25, 2005, 17, pp. 2987-2996.

Yoshida, Toyonobu, "The Future of Thermal Plasma Processing for Coating," Pure & Appl. Chem., vol. 66, No. 6, 1994, pp. 1223-1230.

Kim, Namyong Y. et al., "Thermal Derivatization of Porous Silicon with Alcohols," J. Am. Chem. Soc., Mar. 5, 1997, 119, pp. 2297-2298.

Hua, Fengjun et al., "Organically Capped Silicon Nanoparticles with Blue Photoluminescence Prepared by Hydrosilylation Followed by Oxidation," Langmuir, Mar. 2006, pp. 4363-4370.

Stiles, A.B., Catalyst Supports and Supported Catalysts, Manufacture of Carbon-Supported Metal Catalysts, pp. 125-132, published Jan. 1, 1987, Butterworth Publishers, 80 Montvale Ave., Stoneham, MA 02180.

United States Patent and Trademark Office, Advisory Action mailed Jul. 21, 2011, for U.S. Appl. No. 12/474,081, 3 pgs.

"Platinum Group Metals: Annual Review 1996" (Oct. 1997). Engineering and Mining Journal, p. 63.

U.S. Appl. No. 13/291,983, filed Nov. 8, 2011, for Layman et al.
U.S. Appl. No. 12/152,084, filed May 9, 2008, for Biberger.
U.S. Appl. No. 13/028,693, filed Feb. 16, 2011, for Biberger.
U.S. Appl. No. 12/943,909, filed Nov. 10, 2010, for Layman.
U.S. Appl. No. 12/152,111, filed May 9, 2008, for Biberger et al.
U.S. Appl. No. 12/151,830, filed May 8, 2008, for Biberger et al.
U.S. Appl. No. 12/968,248, filed Dec. 14, 2010, for Biberger.
U.S. Appl. No. 12/968,245, filed Dec. 14, 2010, for Biberger.
U.S. Appl. No. 12/968,241, filed Dec. 14, 2010, for Biberger.
U.S. Appl. No. 12/968,239, filed Dec. 14, 2010, for Biberger.
U.S. Appl. No. 12/969,128, filed Dec. 15, 2010, for Biberger.
U.S. Appl. No. 12/962,463, filed Dec. 7, 2010, for Leamon.
U.S. Appl. No. 12/961,030, filed Dec. 6, 2010, for Lehman.
U.S. Appl. No. 12/961,108, filed Dec. 6, 2010, for Lehman.
U.S. Appl. No. 12/961,200, filed Dec. 6, 2010, for Lehman.
U.S. Appl. No. 12/968,253, filed Dec. 14, 2010, for Biberger.
U.S. Appl. No. 12/968,235, filed Dec. 14, 2010, for Biberger.
U.S. Appl. No. 12/969,306, filed Dec. 15, 2010, for Lehman et al.
U.S. Appl. No. 12/969,447, filed Dec. 15, 2010, for Biberger et al.
U.S. Appl. No. 12/969,087, filed Dec. 15, 2010, for Biberger.
U.S. Appl. No. 12/962,533, filed Dec. 7, 2010, for Yin et al.
U.S. Appl. No. 12/962,523, filed Dec. 7, 2010, for Yin et al.
U.S. Appl. No. 12/001,643, filed Dec. 11, 2007, for Biberger et al.
U.S. Appl. No. 12/474,081, filed May 28, 2009, for Biberger et al.
U.S. Appl. No. 12/001,644, filed Dec. 11, 2007, for Biberger et al.
U.S. Appl. No. 12/969,457, filed Nov. 15, 2010, for Leamon et al.
U.S. Appl. No. 12/969,503, filed Nov. 15, 2010, for Leamon et al.
U.S. Appl. No. 12/954,813, filed Nov. 26, 2010, for Biberger.
U.S. Appl. No. 12/954,822, filed Nov. 26, 2010, for Biberger.
U.S. Appl. No. 13/033,514, filed Feb. 23, 2011, for Biberger et al.

* cited by examiner

METHOD AND SYSTEM FOR FORMING PLUG AND PLAY METAL COMPOUND CATALYSTS

RELATED APPLICATION(S)

This patent application claims priority under 35 U.S.C. §119(e) of the co-pending U.S. Provisional Patent Application Ser. No. 60/999,057, filed Oct. 15, 2007, and entitled "Nano Particle Catalysts" which is hereby incorporated by reference in its entirety.

BACKGROUND OF THE INVENTION

In the oil refining and fine chemical industries, catalysts are required to transform one chemical or one material into another. For example, to make cyclohexane from benzene, benzene is passed through porous ceramic supports that have been impregnated with catalysts designed and configured to hydrogenate it into cyclohexane. In one particular process, platinum is nitrated and impregnated onto supports in the wet chemical process 100 shown in FIG. 1. A platinum group metal, such as platinum, osmium, ruthenium, rhodium, palladium or iridium, is collected in step 101. For the sake of brevity, platinum will be discussed herein but it will be apparent to those of ordinary skill in the art that different platinum group metals can be used to take advantage of their different properties. Since blocks of elemental platinum are not useable as a catalyst, the platinum is nitrated in the step 102, forming a salt, specifically $PtNO_3$. The nitration is typically performed using well known methods of wet chemistry. The $PtNO_3$ is dissolved into a solvent such as water in a step 103, causing the $PtNO_3$ to dissociate into Pt+ and $NO_3-$ ions. In the step 104, the salt is adsorbed onto the surfaces of supports 104B through transfer devices 104A, such as pipettes. An example of a support 104B is shown in FIG. 2. Generally, a support 104B is a highly porous ceramic material that is commercially available in a vast array of shapes, dimensions and pore sizes to accommodate particular requirements of a given application. The supports 104B are dried to remove water then transferred to an oven for an air calcining step 105. In the oven, the supports 104B are exposed to heat and optionally pressure that causes the Pt+ to coalesce into elemental Pt particles on the surfaces of the supports 104B. In the step 106, end product catalysts are formed. The end product is a support 104B that is impregnated with elemental platinum. These supports are generally used in catalytic conversion by placing them in reactors of various configurations. For example, benzene is passed through the supports 104B which convert the benzene into cyclohexane in the fine chemical industry. In the oil refining industry, the supports are used in a similar fashion. The process steps are used to convert crude oil into a useable fuel or other desirable end product. The process described in FIG. 1 has opportunities for improvement. Although the platinum sticks sufficiently well to the surface of the support 104b, platinum atoms begin to move and coalesce into larger particles at the temperatures that catalysis generally occurs. It is understood that the effectiveness and activity of a catalyst are directly proportional to the size of the catalyst particles on the surface of the support. As the particles coalesce into larger clumps, the particle sizes increase, the surface area of the catalyst decreases and the effectiveness of the catalyst is detrimentally affected. As the effectiveness of the catalyst decreases, the supports 104B must be removed from the reactors and new supports added. During the transition period, output is stopped and overall throughput is adversely affected. Also, platinum group metal catalysts are very expensive, and every addition of new supports comes at great cost. What is needed is a plug and play catalyst that is usable in current oil refineries and fine chemical processing plants, allowing an increase in throughput and decrease in costs.

SUMMARY OF THE INVENTION

A method of making a metal compound catalyst comprises providing a quantity of nanoparticles, wherein at least some of the nanoparticles comprise a first portion comprising catalyst material bonded to a second portion comprising a carrier, providing a quantity of supports; and impregnating the supports with the nanoparticles. In some embodiments, the supports comprise pores and voids. The catalyst material comprises any among a list of at least one metal, at least one metal alloy, and any combination thereof. Also, the catalyst material comprises any among a list of nitrogen, carbon, phosphorous, hydrogen, oxygen, sulfur, and any combination thereof. Preferably, providing a quantity of nanoparticles comprises loading a quantity of catalyst material and a quantity of carrier into a plasma gun in a desired ratio, vaporizing a quantity of catalyst and quantity of carrier, thereby forming a vapor cloud quenching the vapor cloud, thereby forming precipitate nanoparticles, and injecting a co-reactant such that the co-reactant will react with one of the vapor cloud, the first portion of the precipitate nanoparticles and any combination thereof. The co-reactant is injected into a substantially low oxygen environment. The co-reactant comprises any among a list of a carbon compound, a nitrogen compound, a phosphorous compound, and oxygen compound, a hydrogen compound, a sulfur compound, and any combination thereof. Preferably, the carrier comprises an oxide such as silica, alumina, yttria, zirconia, titania, ceria, baria, and any combination thereof. Preferably, impregnating the supports comprises suspending the nanoparticles in a solution, thereby forming a suspension, and mixing the suspension with a quantity of the supports. Alternatively, impregnating the supports comprises suspending the nanoparticles in a solution, thereby forming a suspension, and mixing the suspension with a slurry having supports suspended therein. The slurry comprises any among an organic solvent, an aqueous solvent, and a combination thereof. Preferably, the method further comprises drying the supports. The method further comprises exposing the supports to any one of heat, pressure or a combination thereof, thereby calcining the nanoparticles onto the supports.

A system for forming a metal compound catalyst comprises means for providing a quantity of nanoparticles, wherein at least some of the nanoparticles comprise a first portion of catalyst material bonded to a second portion of carrier, means for collecting the nanoparticles, means for forming a suspension by mixing the nanoparticles into a liquid, and means for combining the suspension with a quantity of supports, thereby supports with the dispersion. Preferably, the catalyst material comprises any among a list of at least one metal, at least one metal alloy, and any combination thereof. Also, the catalyst material comprises any among a list of nitrogen, carbon, phosphorous, hydrogen, oxygen, sulfur, and any combination thereof. Preferably, the means for providing a quantity of nanoparticles comprises means for loading a quantity of catalyst material and a quantity of carrier into a plasma gun in a desired ratio means for vaporizing the quantity of catalyst material and carrier material in a reaction chamber, thereby forming a reactant vapor cloud means for quenching the reactant vapor cloud thereby forming solid nanoparticles, and means for injecting a co-reactant such that the co-reactant will react with any among the vapor cloud, the first portion of the nanoparticles, and any combination thereof. Preferably, the means for injecting a co-reactant comprises means for injecting the co-reactant into a substantially low oxygen environment. The co-reactant comprises any among a list of a carbon compound, a nitrogen compound, a phosphorous compound, an oxygen compound, a hydrogen compound, and any combination thereof. The system further comprises means for drying the supports. Preferably, the system further comprises means for exposing the supports to any among heat, pressure, and a combination thereof thereby calcining the nanoparticles onto the supports. Preferably, means for combining the suspension with supports comprises means for impregnating supports with the suspension. Alternatively, the means for combining the suspension with supports comprises means for mixing the suspension with a slurry having supports. The slurry comprises any among an organic solvent, an aqueous solvent, and any combination thereof.

BRIEF DESCRIPTION OF THE DRAWINGS

The invention is better understood by reading the following detailed description of an exemplary embodiment in conjunction with the accompanying drawings.

DETAILED DESCRIPTION OF THE INVENTION

Reference will now be made in detail to implementations of the present invention as illustrated in the accompanying drawings. The drawings may not be to scale. The same reference indicators will be used throughout the drawings and the following detailed description to refer to identical or like elements. In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application, safety regulations and business related constraints, and that these specific goals will vary from one implementation to another and from one developer to another. Moreover, it will be appreciated that such a development effort will be a routine undertaking of engineering for those of ordinary skill in the art having the benefit of this disclosure.

The following description of the invention is provided as an enabling teaching which includes its best currently known embodiment. One skilled in the relevant arts, including but not limited to chemistry and physics, will recognize that many changes can be made to the embodiment described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present inventions are possible and may even be desirable in certain circumstances, and are a part of the present invention. Thus, the following description is provided as illustrative of the principles of the present invention and not in limitation thereof, since the scope of the present invention is defined by the claims. The terms "nanoparticle," "nanoparticle powder," and "nano powder" are generally understood by those of ordinary skill to encompass a quantity of material comprising particles on the order of nanometers in diameter, as described herein. The term "metal compound" is generally understood by those of ordinary skill to encompass a compound comprising at least one metal and at least one non metal.

Figure 3:
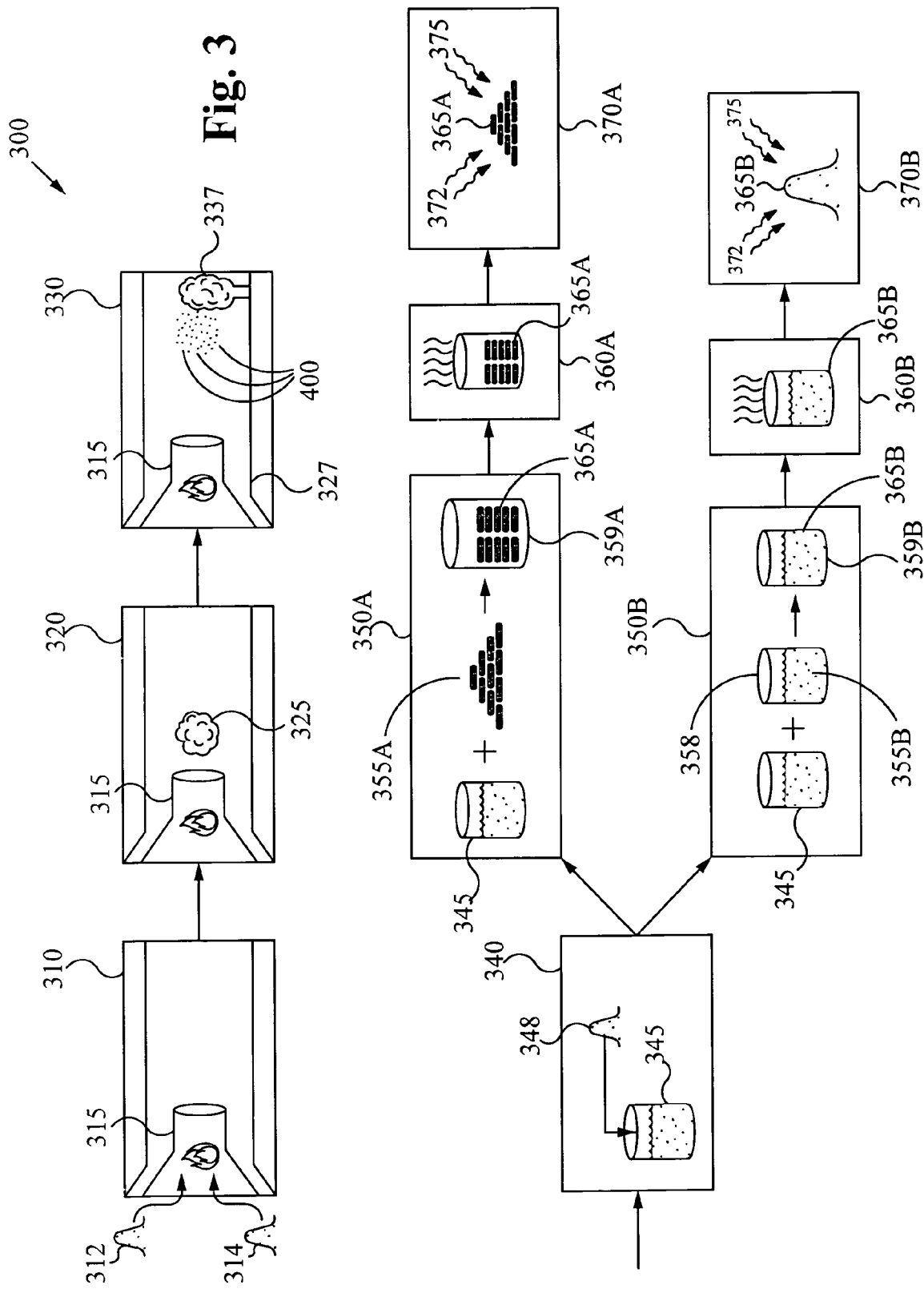
FIG. 3 shows the preferred embodiment of a novel process for forming a support for use in heterogeneous catalysis.

FIG. 3 illustrates the inventive steps for a process 300 of forming a "plug and play" catalyst for use in such industries as chemical manufacturing and oil refining. The method begins at the step 310. A quantity of a catalyst material 312 is loaded into a plasma gun 315. Preferably, the catalyst material 312 comprises a transition metal. Transition metals (TM) and their compounds are able to provide excellent catalytic properties. Although transition metals are described, all metals are contemplated. Other metals, such as platinum group metals and poor metals, also exhibit catalytic properties. Generally, transition metals comprise scandium, titanium, chromium, vanadium, manganese, iron, cobalt, nickel, copper, zinc, yttrium, zirconium, niobium, molybdenum, cadmium, tantalum, tungsten, and mercury. Poor metals comprise aluminum, germanium, gallium, tin, antimony, lead, indium, tellurium, polonium and bismuth. Platinum group metals comprise ruthenium, rhodium, palladium, osmium, iridium, and platinum. The catalyst material 312 is able to comprise more than one starting metal. By way of example, the material 312 is a single alloy comprising multiple metals. Alternatively, the catalyst material 312 comprises multiple homogenous metals or metal compounds such as oxides. Particularly, metals are used in heterogeneous catalysis. Heterogeneous catalysts provide a surface for the chemical reaction to take place on or provide an activation point for chemical reactions. Also, in step 310, a quantity of carrier material 314 is loaded into the plasma gun 315. In some embodiments, the carrier material 314 is an oxide. By way of example, oxides such as Alumina ($Al_2O_3$), Silica ($SiO_2$), Zirconia ($ZrO_2$), Titania ($TiO_2$), Ceria ($CeO_2$) Baria (BaO), and Yttria ($Y_2O_3$) can be used. Other useful oxides will be apparent to those of ordinary skill. In some embodiments, the catalyst material 312 and carrier material 314 are loaded manually into a hopper (not shown) which automatically loads the materials into the plasma gun 315. In alternate embodiments, an automated system is able to load the catalyst material 312 and oxide carrier 314 into the plasma gun 315. The ratio of the TM to the carrier can be adjusted to meet particular demands of a given application. Next, in step 320, the plasma gun 315 vaporizes the catalyst material 312 along with the carrier 314 to form a vapor cloud 325. The vapor cloud will comprise both the catalyst material, for example TM, and the carrier in the ratio that was loaded into the plasma gun 315 in step 310.

Figure 4A:
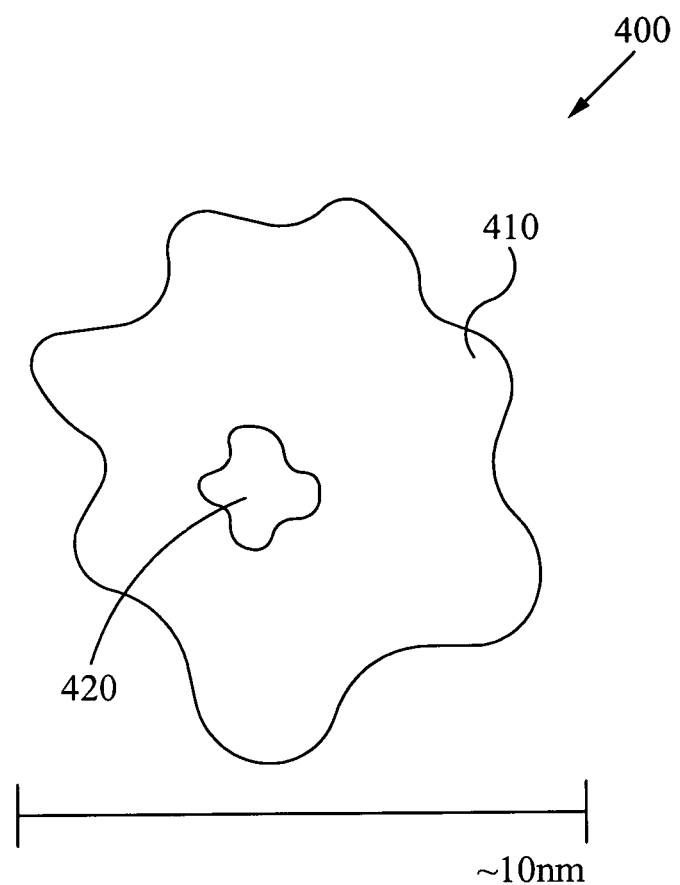
FIG. 4A shows an example of a nanoparticle formed as part of the process of FIG. 3.

Still referring to FIG. 3, the resulting vapor cloud 325 is then put through a quenching step 330. Preferably, the quenching step occurs in a highly turbulent quench chamber 327 to facilitate rapid, even, consistent quenching of the vapor cloud 325 into precipitate nanoparticles. Such a rapid quench chamber is described in detail in U.S. Patent Publication No. 2008/0277267, and is hereby incorporated by reference. As the gaseous TM and carrier cool, they solidify into nanoparticles. An example of a resulting nanoparticle 400 is shown in FIG. 4A. As shown, the nanoparticle comprises a portion of carrier 410, and a portion of TM catalyst 420. The ratio of size between the TM catalyst 420 and carrier 410 will generally be determined by the ratio of the starting quantities of catalyst material 312, such as TM and carrier material 314 in the step 310 of FIG. 3. To further enhance the catalytic effects of the TM, the TM is combined with a nonmetal to form a metal compound. Preferably, the combination is effectuated by injecting a co-reactant, in this example a co-reactant gas 337 into the reaction chamber 327. Preferably, the co-reactant 337 is injected as a gas post plasma. In some embodiments, the injected gas 337 is organic. Alternatively, the injected gas is an oxygen compound, a hydrogen compound, a nitrogen compound, a phosphorous compound, a sulfur compound, or a carbon containing compound. Preferably, as the particles 400 precipitate, the gas 337 dissociates into its component elements that then react with the metal portion 420 of the nanoparticle 400. Alternatively, a chemical reaction occurs between the gas to the metal portion 420 of the nanoparticle 400. As described, the gas 337 interacts with the metal portion 420 of the nanoparticles 400 after the nanoparticles have precipitated from the vapor cloud 325. Interaction between the gas 337 and the vapor cloud 325 itself is also contemplated. The gas 337 dissociates into its constituent elements which then react with the catalyst material 312 in its vapor state before precipitation. Alternatively, the gas 337 reacts with the catalyst material 312 without dissociating. It is understood the reaction of the gas 337 with the catalyst material 312 or metal portion 420 of the nanoparticle 400 is able to occur before, during, or after precipitation, or may begin before precipitation and complete after precipitation. By way of example, and not intended to be in any way limiting, if the end catalyst product desired is the metal compound tungsten carbide, the starting catalyst material 312 will be a quantity of tungsten. Along with a quantity of a carrier 314, such as alumina, the quantity of tungsten is loaded into the plasma gun 315. After vaporization, nanoparticles of tungsten will collide with nanoparticles of alumina and form the nanoparticles 400. Further down the reaction chamber 327 from the plasma gun 315, methane vapor 337 ($CH_4$) is injected. It is important to note that the methane vapor 337 is injected into the reaction chamber 327 where the temperature is sufficient to dissociate methane into its components, carbon and hydrogen. Alternatively, the methane reacts with the tungsten. As described above, the reaction is able to occur before, during, after, or throughout the precipitation of tungsten- on-alumina nanoparticles 400. Also, to avoid combustion of the methane into carbon dioxide and water, rather than elemental carbon and hydrogen, a substantially low oxygen environment is provided for the reaction chamber 327. A low oxygen reaction chamber is described in detail in [US APPLICATION # FOR SDC 03200] and is hereby incorporated by reference. When the methane dissociates, the hydrogen atoms form hydrogen vapor. The carbon atom is known to be extremely reactive, and will carburize the tungsten forming tungsten carbide. Alternatively, a chemical reaction will react the methane to the tungsten. Referring to the example nanoparticle 400 in FIG. 4, the catalyst portion 420 is the metal compound tungsten carbide. It can be appreciated by those of ordinary skill in the art that other compound catalysts are able to be formed by the process 300. If a different metal compound, such as a metal nitride is the desired final product, the desired metal will be loaded into the plasma gun 315 and ammonia ($NH_3$) rather than methane will be injected into the reaction chamber 327. As ammonia dissociates into its constituent elements, they will react with the desired metal to form a metal nitride. It will be apparent to those of ordinary skill that many combinations of metals and nonmetals are able to be combined in the manner described, and the two examples given are not intended in any way to limit the scope of the disclosure. As new catalysts are required for new chemical processes, the process 300 is able to be applied through a routine, although possibly time consuming engineering endeavor. The particles 400 will generally be in the range of 0.5 to 200 nm in size, and can be as small as a molecular length of the catalyst portion 420 and as large as would be achievable by ball milling. The particle size is able to be varied with varying starting materials, vaporization speeds, quench speeds and plasma temperatures.

U.S. Pat. No. 5,989,648 to Phillips discloses a method for forming nanoparticle metal catalysts on carriers. However, referring back to FIG. 3, it is important to note that nanoparticles 400 such as the one shown in FIG. 4 are not generally compatible with existing processes for chemical conversion. For compatibility with existing processes, the nanoparticles 400 are bonded to a support. To that end, more steps are taken to bring the nanoparticles 400 to a useable form. In some embodiments, the process 300 continues with step 340, where the nanoparticles 400 are combined with a liquid to form a dispersion 345. Preferably, a liquid that will not react with the TM or the carrier material is used. Some appropriate liquids are aqueous solutions or organic solutions employing solvents such as alcohols, ethers, hydrocarbons, esters, amines, or the like. Since the nanoparticles 400 are small, other precautions are generally taken to ensure that they suspend evenly within the dispersion. To that end, an adjunct 348 is able to be added to the dispersion. The adjunct 348, also referred to commonly in the art as a surfactant or dispersant, adheres to the nanoparticles 400 and causes them to repel each other, thereby causing the nanoparticles 400 to suspend evenly in the dispersion 345. The dispersion 345 is also referred to as a suspension.

Figure 1:
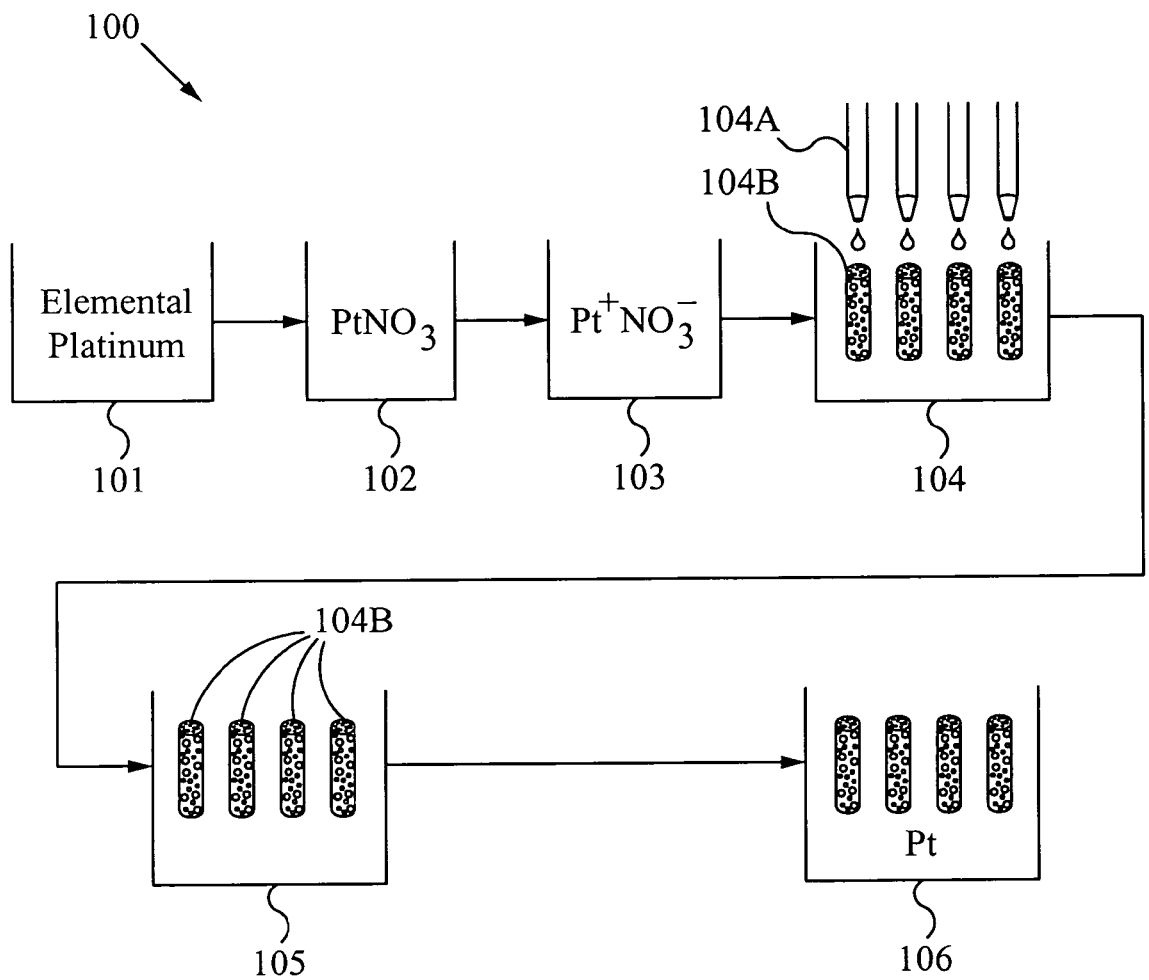
FIG. 1 prior art illustrates an existing process for forming a useful support for use in heterogenous catalysis.
Figure 2:
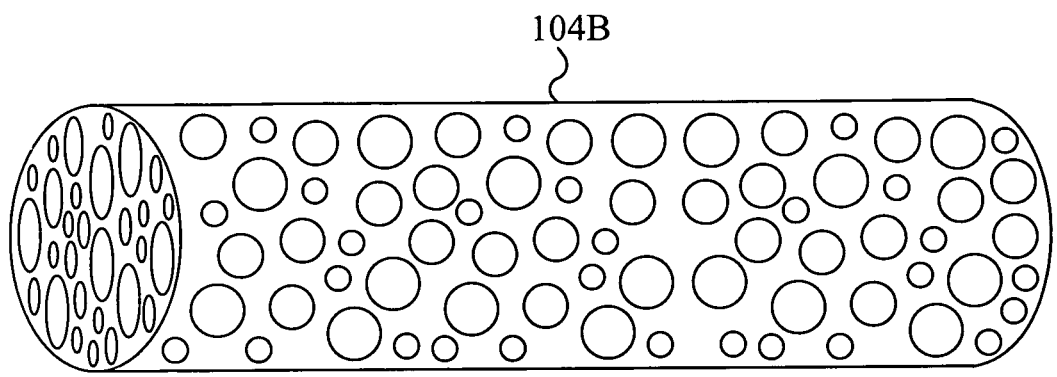
FIG. 2 prior art shows a porous support generally used as a support in heterogeneous catalysis.

To bring the nanoparticles 400 closer to a usable catalyst, the nanoparticles 400 are impregnated onto supports 355. The supports 355 are also known to those skilled in the relevant art as porous oxides. Alternatively, the supports 355 are also referred to as extrudates because they are generally made using an extrusion process. The supports 355 are similar to the supports 104b in FIGS. 1 and 2. Such supports have found utility due to their highly accessible and large surface area, as high as 250 $m^2$/g. In alternative embodiments, a macroscopic support particle is able to be used. In such an embodiment, the size of the macroscopic support particle is selected to provide maximum surface area to which nanoparticles 400 are bonded or fixed. The step 350A shows the preferred embodiment of achieving the impregnation. The dispersion 345 is combined with a quantity of substantially dry porous supports 355A to form a mixture 359A. Alternatively, as shown in the step 350B, the dispersion 345 is combined with a slurry 358 having macroscopic support particles 355B suspended therein, thereby forming the mixture 359B. The slurry 358 is able to be a suspension of water, alcohol, or any suitable organic or inorganic liquid which will not react with the macroscopic supports 355B or nanoparticles 400. In the step 350A, capillary forces will draw in the dispersion 345, and in turn the nanoparticles 400, into the various voids and pores within the structure of the porous supports 355A, thereby forming impregnated porous supports 365A. To aid in the impregnation, the mixture can be agitated or subjected to heat or pressure. In the step 350B, nanoparticles 400 come to rest on the surfaces of macroscopic supports thereby forming impregnated macro supports 365B. In some embodiments, the steps 350A or 350B are repeated at least once for enhanced impregnation.

Figure 4B:
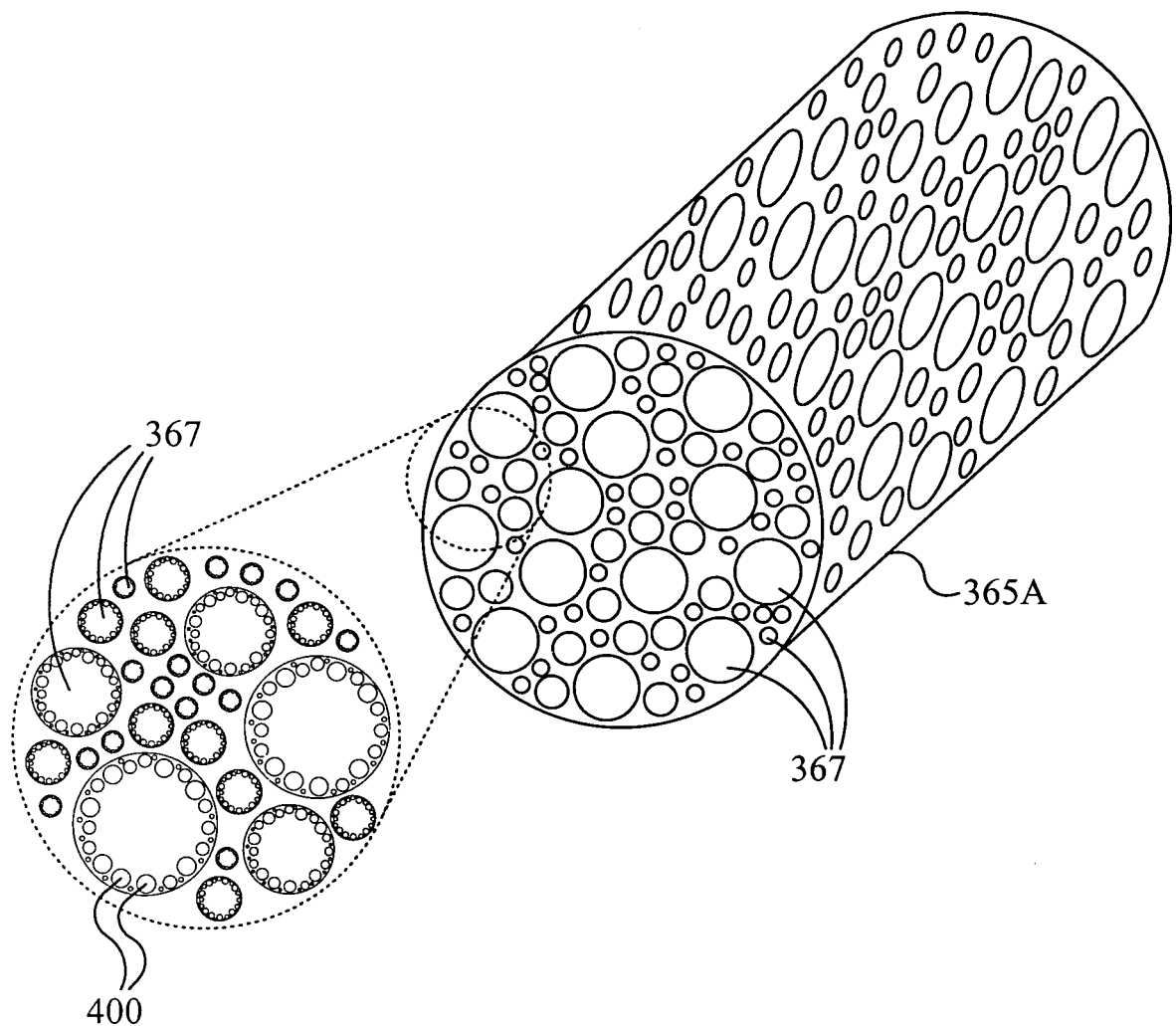
FIG. 4B shows a close up of an impregnated porous support.
Figure 4C:
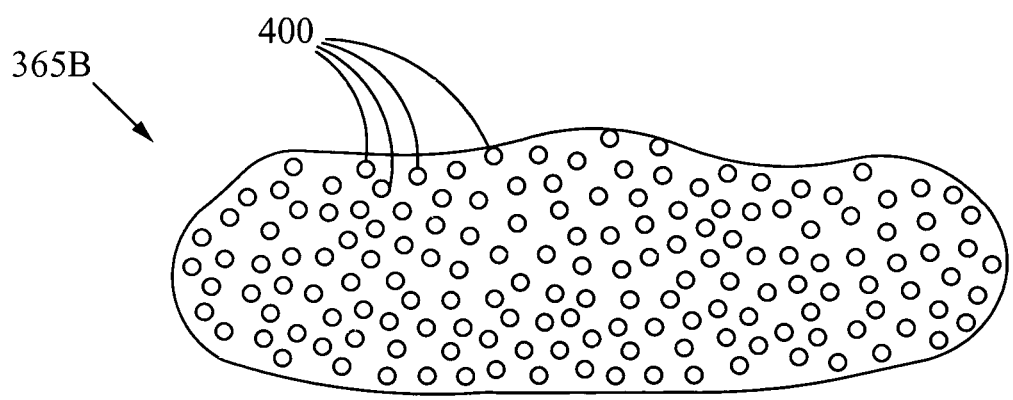
FIG. 4C shows a close up of an impregnated macro support.

Next, in the steps 360A and 360B, the impregnated porous supports 365A or macro supports 365B are allowed to dry. A close up view the impregnated porous support 365A is shown in FIG. 4B. As the liquid in the dispersion 345 evaporates, the nanoparticles 400 settle onto the surface of the support 365A and into the pores 367 within the support 365A. FIG. 4C shows an example of an impregnated macro support 365B. As the liquids in the dispersion 345 and slurry 358 dry, nanoparticles 400 settle onto the surface of the macro support 365B. When the impregnated porous supports 365A or macro supports 365B dry, electrostatic interactions and other non covalent forces between the nanoparticles 400 and the porous supports 365A or macro supports 365B effectuate some adhesion. Advantageously, such forces cause the nanoparticles 400 to stick onto the surfaces and pores 367 of the supports 365A or 365B, and effectuate transfer of the supports 365 through the remainder of the process 300. Referring back to FIG. 3, a calcining step 370A or 370B is performed to form oxide-oxide bonds between the carrier portion 410 of the nanoparticles 400 and the impregnated supports 365A or 365B by exposing them to heat 372, pressure 375, or a combination thereof. The calcining temperature is generally from 350 to 1000 degrees centigrade, and the pressure is on the order of ambient atmosphere to several atmospheres. Calcining is able to occur in an inert environment or in air. For optimum oxide-oxide bonds, the carrier material 314 is chosen to correspond to the material of which the support 365A or 365B is comprised. By way of example, if the carrier material 314 is alumina, then the support 365A or 364B preferably comprises alumina, although dissimilar oxides are also contemplated. Due to the physical and chemical bond between the supports 365A and 365B and the nanoparticles 400, islands of nanoparticles that are bonded, fixed or otherwise pinned to the surfaces of the supports 365A or 365B will not migrate and coalesce during catalytic conversion. The surface area for catalysis remains high, and therefore the catalytic activity remains high. In effect, operations such as fine chemical plants and oil refineries will not be required to stop operations and swap out ineffective catalyst supports with fresh catalyst supports with the same frequency as existing processes, thereby increasing throughput at the plants and refineries and reducing their overall cost of operation.

Figure 5:
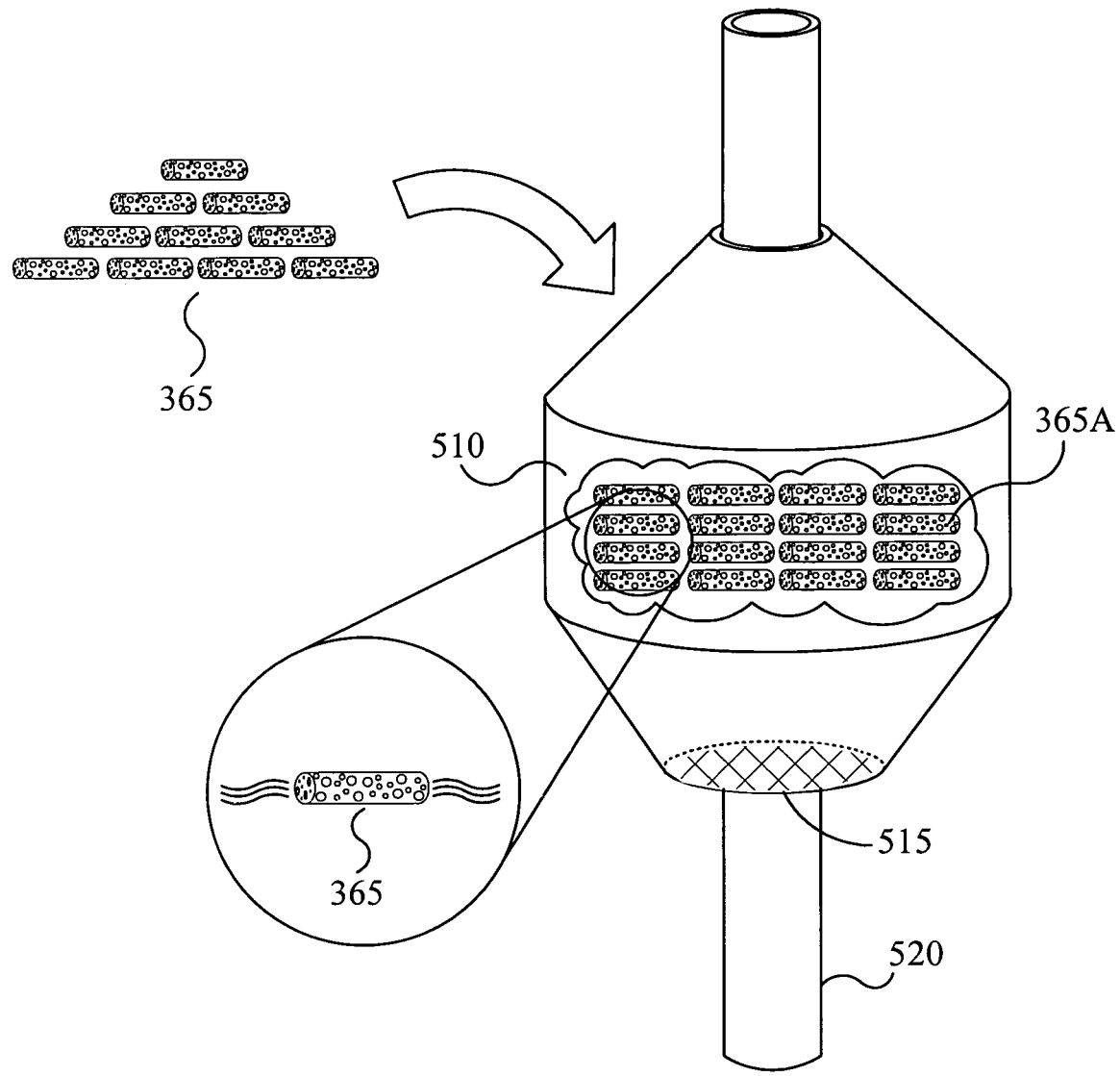
FIG. 5 shows an example of the supports being used as heterogeneous catalysts.

FIG. 5 shows an example of the impregnated porous supports 365A being used in the fine chemical industry to hydrogenate benzene into cyclohexane. Macro supports 365B are able to be used as well. Although this example details use in the fine chemical industry, it will be apparent to those of ordinary skill in the arts of chemistry, chemical engineering, or the like that any process using heterogeneous catalysis is able to benefit from this disclosure. An amount of impregnated porous supports 365A is loaded into a reactor 510. Preferably, the reactor 510 has a mesh opening 515 on one end wherein the meshing has a smaller opening pitch than the size of the supports 365 such that the supports 365 do not fall through the opening 515. Benzene is passed into the vat 510 via the conduit 520. As the benzene passes through the vat 510, the benzene fills into the voids and pores of the supports 365A.

Figure 5A:
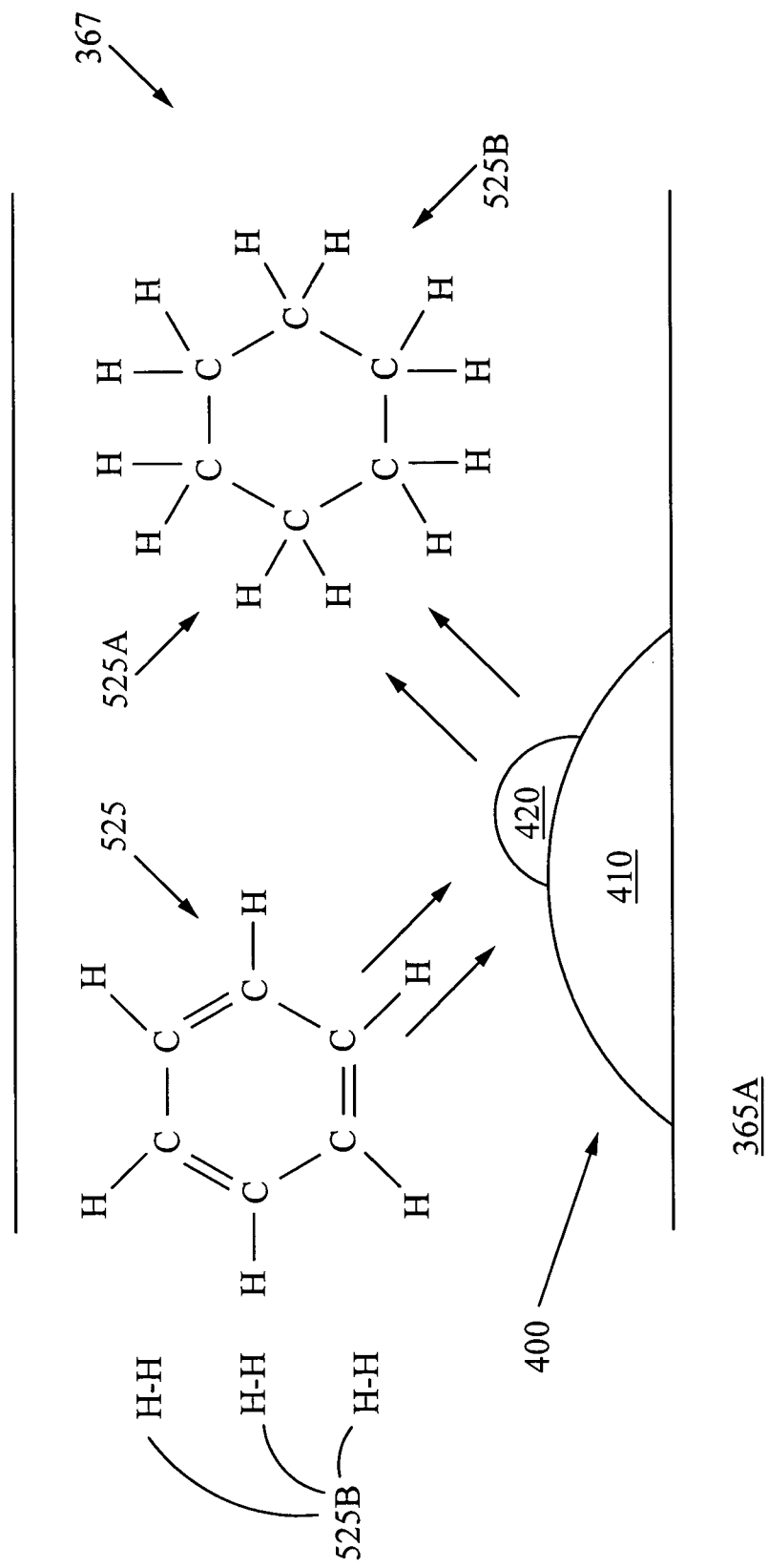
FIG. 5A shows the hydrogenation of benzene into cyclohexane.

FIG. 5A shows an example of a benzene molecule 525 being hydrogenated into cyclohexane 525A in a cross section of a pore 367. When the benzene molecule 525 comes into contact with the catalyst portion 420 of the nanoparticle 400 that is bonded to the surface of the support 365A, the catalyst portion 420 of the nanoparticle 400 will effectuate hydrogenation of the benzene molecule 525 and hydrogen molecules 525B into cyclohexane 525A.

We claim:
1. A method of making a metal compound catalyst comprising:
 a. providing a quantity of nanoparticles, comprising the steps:
  i. loading a quantity of catalyst material in powder form and a quantity of carrier comprising an oxide into a plasma gun in a desired ratio;
  ii. vaporizing the quantity of catalyst material and the quantity of carrier by the plasma gun, thereby forming a vapor cloud;
  iii. quenching the vapor cloud received from the plasma gun, thereby forming precipitate nanoparticles; and
  iv. injecting a co-reactant into a substantially low oxygen environment such that the co-reactant will react with one of the vapor cloud, the precipitate nanoparticles, and any combination thereof,
 wherein at least some of the nanoparticles comprise a first portion comprising a catalyst material bonded to a second portion comprising a carrier, wherein the carrier comprises an oxide;
 b. providing a quantity of supports comprising a same oxide as in the carrier loaded in the plasma gun;
 c. combining the supports with the nanoparticles; and
 d. forming a structure having the catalyst material bonded with the carrier, wherein the carrier is bonded with the support through an oxide-oxide bond.

2. The method of claim 1 wherein the supports comprise pores and voids.

3. The method of claim 1 wherein the quantity of catalyst material comprises at least one metal, at least one metal alloy, or any combination thereof.

4. The method of claim 1 wherein the quantity of catalyst material comprises nitrogen, carbon, phosphorous, hydrogen, oxygen, sulphur, or any combination thereof.

5. The method of claim 1 wherein the co-reactant comprises a carbon compound, a nitrogen compound, a phosphorus compound, an oxygen compound, a hydrogen compound, a sulfur compound, or any combination thereof.

6. The method of claim 1 wherein the carrier loaded into the plasma gun comprises silica, alumina, yttria, zirconia, titania, ceria, baria, or any combination thereof.

7. The method of claim 1 wherein combining the supports with the nanoparticles comprises:
 a. suspending the nanoparticles in a solution, thereby forming a suspension; and
 b. mixing the suspension with the quantity of supports.

8. The method of claim 1 wherein combining the supports with the nanoparticles comprises:
 a. suspending the nanoparticles in a solution, thereby forming a suspension; and
 b. mixing the suspension with a slurry having supports suspended therein.

9. The method of claim 8 wherein the slurry comprises an organic solvent, an aqueous solvent, or a combination thereof.

10. The method of claim 1 further comprising drying the supports.

11. The method of claim 1 further comprising exposing the supports to any one of heat, pressure or a combination thereof, thereby calcining the nanoparticles onto the supports.

12. A supported catalyst, comprising:
 a. a support structure comprising an oxide; and
 b. a nanoparticle, wherein the nanoparticle has been quenched from a vapor cloud induced by a plasma gun from a catalyst material and a carrier material comprising a same oxide as in the support structure in powder form and reacted with a co-reactant in a substantially low oxygen environment, the nanoparticle comprising a catalyst portion and a carrier portion, the carrier portion being bonded through an oxide-oxide bond to the support structure.

13. The supported catalyst of claim 12 wherein the catalyst portion comprises a metal, a metal compound, a metal alloy, or any combination thereof.

14. The supported catalyst of claim 12 wherein the carrier portion comprises silica, alumina, yttria, zirconia, titania, ceria, baria, or any combination thereof.

15. The method of claim 7 wherein the supports are dry porous supports.

16. The method of claim 8 wherein the supports are macroscopic support particles.

17. A method of making a supported metal compound catalyst comprising:
   a. providing a quantity of nanoparticles for combining with a quantity of supports, comprising the steps:
      i. loading a quantity of catalyst material in powder form into a plasma gun and loading a quantity of a carrier comprising an oxide into the plasma gun in a desired ratio, wherein the catalyst comprises a metal;
      ii. vaporizing the quantity of catalyst material and vaporizing the quantity of carrier using the plasma gun, thereby forming a vapor cloud;
      iii. receiving the vapor cloud from the plasma gun by a quench chamber;
      iv. quenching the vapor cloud received from the plasma gun, thereby forming a quantity of precipitate nanoparticles;
      v. injecting a co-reactant into a substantially low oxygen environment such that the co-reactant will react with one of the vapor cloud, the precipitate nanoparticles, and any combination thereof;
   wherein at least some of the nanoparticles comprise a first portion comprising a catalyst material bonded to a second portion comprising a carrier; and
   b. impregnating the at least some of the nanoparticles into a quantity of dry porous supports comprising a porous oxide, wherein the porous oxide comprises a same oxide as the carrier loaded in the plasma gun, comprising the steps:
      i. combining the at least some of the nanoparticles with a liquid dispersant to form a dispersion;
      ii. combining the dispersion with the quantity of dry porous supports to create a mixture;
      iii. subjecting the mixture to one of agitating, heating, and applying pressure;
      iv. allowing the mixture to dry, thereby creating impregnated supports;
      v. calcining the impregnated supports by exposing them to one of heat and pressure;
   thereby making a supported metal compound catalyst having a structure in which the support is bonded with the carrier through an oxide-oxide bond and the carrier is bonded with the catalyst material.

18. A method of making a supported metal compound catalyst comprising:
   a. providing a quantity of nanoparticles for combining with a quantity of supports, comprising the steps:
      i. loading a quantity of catalyst material comprising a metal into a plasma gun and loading a quantity of a carrier comprising an oxide in powder form into the plasma gun in a desired ratio, wherein the carrier comprises an oxide;
      ii. vaporizing the quantity of catalyst material and vaporizing the quantity of carrier using the plasma gun, thereby forming a vapor cloud;
      iii. receiving the vapor cloud from the plasma gun by a quench chamber;
      iv. quenching the vapor cloud received from the plasma gun, thereby forming a quantity of precipitate nanoparticles;
      v. injecting a co-reactant into a substantially low oxygen environment such that the co-reactant will react with one of the vapor cloud, the precipitate nanoparticles, and any combination thereof;
   wherein at least some of the nanoparticles comprise a first portion comprising a catalyst material bonded to a second portion comprising a carrier; and
   b. impregnating the at least some of the nanoparticles into a quantity of macroscopic support particles comprising a same oxide as in the carrier loaded in the plasma gun, comprising the steps:
      i. combining the at least some of the nanoparticles with a liquid dispersant to form a dispersion;
      ii. combining a quantity of macroscopic support particles with a selected liquid to create a slurry, wherein the selected liquid comprises one of water, alcohol, organic liquid, and inorganic liquid, and wherein the selected liquid does not react with the macroscopic supports and does not react with the at least some of the nanoparticles;
      iii. combining the dispersion with the slurry to create a mixture;
      iv. subjecting the mixture to one of agitating, heating, and applying pressure;
      v. allowing the mixture to dry, thereby creating impregnated supports;
      vi. calcining the impregnated supports by exposing them to one of heat and pressure;
   thereby making a supported metal compound catalyst in which the support is bonded with the carrier through an oxide-oxide bond and the carrier is bonded with the catalyst material.

19. The method of claim 1, wherein the nanoparticles are bonded to the supports.

* * * * *